United States Patent
Silva

(10) Patent No.: US 6,214,235 B1
(45) Date of Patent: Apr. 10, 2001

(54) PROCESS FOR REMOVAL OF QUATERNARY AMMONIUM SALT

(75) Inventor: James Manio Silva, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/055,461

(22) Filed: Apr. 6, 1998

(51) Int. Cl.$^7$ .................... B01D 15/00; B01D 15/04
(52) U.S. Cl. ............................ 210/692; 210/694
(58) Field of Search ..................... 210/692, 694

(56) References Cited

U.S. PATENT DOCUMENTS

| | | | |
|---|---|---|---|
| 4,297,220 | 10/1981 | Meitzner et al. | 210/690 |
| 4,303,704 | 12/1981 | Couduvelis et al. | 210/688 |
| 4,450,057 | 5/1984 | Kelly | 210/681 |
| 5,759,406 | * 6/1998 | Phelps et al. | 210/692 |

FOREIGN PATENT DOCUMENTS

| 3115937 | 11/1982 | (DE) . |
|---|---|---|
| 0697396 | 2/1996 | (EP) . |

OTHER PUBLICATIONS

G. O. Nevstad et al., "Solvent Properties of Dichloromethane. II. the Reactivity of Dichloromethane Toward Amines", Acta Chemical Scandinavica, vol. B38, 1984, pp. 469–477, XP002109466.

Pecsok et al., Journal of the American Chemical Society, vol. 77, Mar. 20, 1955, pp. 1489–149.

* cited by examiner

*Primary Examiner*—Ivars Cintins
(74) *Attorney, Agent, or Firm*—Noreen C. Johnson; Douglas E. Stoner

(57) ABSTRACT

The present invention relates to a process to remove quaternary ammonium salt (QS), from brine solution. The process uses an adsorbent selected from the group consisting of activated carbon and pyrolyzed sulfonated polystyrene divinylbenzene resin, or mixtures thereof which aids in removing the quaternary ammonium salt (QS). The process can be generally carried out at a temperature ranging from about −10° C. to about 90° C., at a pH ranging from about 1 to about 13.

15 Claims, No Drawings

PROCESS FOR REMOVAL OF QUATERNARY AMMONIUM SALT

FIELD OF THE INVENTION

The present invention relates to a process for the removal of quaternary ammonium salts (QS) from a brine solution.

BACKGROUND OF THE INVENTION

Many processes used to manufacture polymers, plastics, and other chemicals generate brine solutions as byproducts. In some cases, the byproduct brine solution contains one or more quaternary ammonium salts (QS) as an impurity. Such quaternary ammonium salts can form in the chemical manufacturing process by reactions between an aliphatic amine, which is often employed as a catalyst, and a chlorinated hydrocarbon, which is often used as a solvent (Gunnar O. Nevstad and Jon Songstad Acta Chem. Scand., Ser. B, B38(6), 469–77, (1984)). In recycle processes in which the product brine solution is utilized as feedstock to a chlor-alkali plant that uses membrane electrolyzer technology, it is important to remove quaternary ammonium salts (QS) from the brine before feeding the brine to the electrolyzers because even small quantities of quaternary ammonium salts (QS) in the feed brine causes elevated cell voltage and foaming in the caustic solution, which is a product of the membrane cell electrolyzer.

Existing brine purification technology is ineffective for removing quaternary ammonium salts from the brine solution. Brines that contain quaternary ammonium salts (QS) are therefore not suitable to be recycled to membrane electrolyzer chlor-alkali plants. There is thus a need for a process that will remove the quatemary ammonium salts from brine solution, before it is recycled to membrane electrolyzers.

SUMMARY OF THE INVENTION

The present invention addresses the above discussed needs by providing a process for removing quaternary ammonium salts (QS) from brine solution generated during the manufacture of polymers, plastics, polycarbonates, and other chemicals, which utilize brine solution and an organic solvent phase.

The present invention provides a process to remove quaternary ammonium salts (QS) from brine solution comprising contacting the quaternary ammonium salts (QS) containing brine solution with an adsorbent at a temperature ranging from about −10° C. to about 90° C., at a pH from about 1 to about 13, and at a feed rate from about 2 to about 40 bed volumes per hour.

DETAILED DESCRIPTION

The process of the present invention removes the quaternary ammonium salts (QS) from the brine solution, and the adsorbent used in the process does not release the quaternary ammonium salts (QS) back into the brine solution.

In the present invention the quaternary ammonium salts (QS) is represented by Formula I:

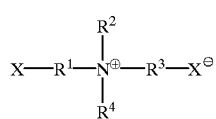

Formula I wherein X is selected from the group consisting of Cl, Br, I, and F; $R^1$ represents $C_{1-3}$ alkylene; and $R^2$, $R^3$, and $R^4$ independently represent a $C_{1-6}$ alkyl radical. A preferred quaternary ammonium salts (QS) is one wherein X is selected from the group consisting of Cl, Br, and I; $R^1$ represents —$CH_2$—; and $R^2$, $R^3$, $R^4$ each independently represent a $C_{1-2}$ alkyl radical. A particularly preferred embodiment of the present invention is one wherein chloromethyl triethylammonium halide is the quaternary ammonium salt (QS) being removed from the brine solution.

Also provided in the present invention is a process wherein the quaternary ammonium salt (QS) concentration ranges from about 0.5 parts per million (ppm) to 100,000 ppm (10%), by weight of the brine solution, and preferably wherein the quaternary ammonium salts (QS) concentration is in the range from about 1 ppm to about 20,000 ppm (2%) ppm by weight of the brine solution. A particularly preferred embodiment provides a process wherein the quaternary ammonium salts' (QS) concentration ranges from about 1 ppm to about 1000 ppm.

Yet another embodiment provides a process wherein the adsorbent is selected from the group consisting of activated carbon, an ion exchange resin, and a carbonaceous synthetic adsorbent, or mixtures thereof. A preferred carbonaceous synthetic adsorbent for the process of the present invention is pyrolyzed sulfonated polystyrene divinylbenzene. This invention comprises exposing the brine solution to either a carbonaceous synthetic adsorbent, activated carbon or a strong acid or weak acid ion exchange resin that is in its alkali metal form, with the sodium form being preferred.

The process of the present invention can be carried out at a temperature ranging from about −10° C. to about 90° C., with the preferred temperature being in the range from about 0° C. to about 80° C., and the most preferred temperature being in the range from about 20° C. to about 80° C. The process of the present invention can be carried out at a pH ranging from about 1 to about 13, with a pH range from about 3 to about 11 being preferred, and a pH range from about 4 to about 10 being most preferred.

Another embodiment of the present invention is one wherein the feed rate of the brine solution is from about 2 to about 40 bed volumes per hour. A preferred embodiment of the present invention is one wherein the feed rate ranges from about 8 to about 32 bed volumes per hour.

The brine solution can be purified in either a batch mode or in a continuous mode, for example by passing the brine over a packed bed of resin beads. Typical commercial brine treatment operating conditions can be used, e.g., from room temperature to about 80° C., using acid or alkaline pH from about 1 to about 13, at feed rates of about 8 to about 32 bed volumes/hr.

As used herein, ion exchange resin is a strong acid or a weak acid ion exchange resin with an alkali metal counter ion, preferably a sodium counter ion. Brine solution, as used in the present invention, comprises at least one solute selected from the group consisting of sodium chloride and potassium chloride, in water, wherein the amount of the solute ranges from about 5 weight percent of water to about its saturation point, at a given operating temperature. A flow rate expressed as 10 bed volumes per hour, for example, indicates that 5 gallons of solution (brine solution in the present case) is contacted with 0.5 gallons of an adsorbent per hour. The term quaternary ammonium salt (QS), in addition to compounds of Formula I, includes hexaalkylguanidinium salts.

EXPERIMENTAL DETAILS

Two types of tests were performed to evaluate the effectiveness of various brine treatments for quaternary ammonium salt (QS) removal. First, batch swirl tests were conducted to screen several adsorbents for their effectiveness in removing the quaternary ammonium salts (QS). Second, several gallons of brine solution were passed over one adsorbent and this purified brine was fed to a lab membrane chlor-alkali cell for evaluation of voltage and foaming.

A. Batch Tests

Examples 1–7

Table 1, below, shows the batch test results. Nominally 100 grams (g) of brine solution (23 g of NaCl in 77 g of distilled water) spiked with 44 ppm of chloromethyl triethylammonium chloride (hereinafater referred to as CTAC), a quaternary ammonium salt (QS) was mixed with 125 milligrams (mg) adsorbent in a 250 milliliters (ml) Erlenmeyer flask. The flasks were swirled overnight in an orbital shaker at 100 revolutions per minute. This solution was filtered using a Buchner funnel under reduced pressure giving a brine filtrate. The residual CTAC. level in the brine filtrate was then measured by ion chromatography (IC).

TABLE 1

| Example | Adsorbent | CTAC Level ppm | % CTAC Removal |
|---|---|---|---|
| 1 | None | 44.0 | 0 |
| 2 | Polystyrene (Rohm and Haas XAD-4) | 40.5 | 8 |
| 3 | Pyrolyzed Sulfonated Polystyrene Divinylbenzene | 4.5 | 90 |
| 4 | Activated Carbon (Calgon Filtrasorb ® 300) | 29.9 | 32 |
| 5 | Activated Carbon (Calgon CPG) | 4.8 | 89 |
| 6 | Strong Acid Ion Exchanger: sodium form (Rohm and Haas Amberlyst ® IRC-131) | 28.2 | 36 |
| 7 | Weak Acid Ion Exchanger: sodium form (Rohm and Haas DP-1) | 33.5 | 24 |

The most effective adsorbents for CTAC. removal pyrolyzed sulfonated polystyrene divinylbenzene (Rohm and Haas Ambersorb® 572 (Example 3), Calgon CPG (Example 5), and Calgon Filtrasorb® 300 (Example 4)), strong acid ion exchanger (Example 6) that is in the sodium form, and weak acid ion exchange resin (Example 7) that is in the sodium form.

B. Continuous Test

Examples 8–10

Table II shows the results of three continuous laboratory cell tests in which brines were fed to a laboratory scale membrane chloralkali electrolyzer. A membrane chlor-alkali electrolyzer has two compartments (an anode compartment and a cathode compartment) separated by a membrane. The brine solution is introduced into the anode compartment, and distilled water is introduced into the cathode compartment, followed by application of electrical current across the membrane electrolyzer. This process electrolyzes the sodium chloride from the brine solution and yields a caustic solution as the liquid product exiting the cathode compartment. Details of this process are given by Curlin, L. C., Bommaraju, T. V., and Hansson, C. B., Alkali and Chlorine Products: Chlorine and Sodium Hydroxide, Kirk-Othmer Encyclopedia of Chemical Technology, Fourth Edition, Volume 1, pp. 938–1025 (1991).

Cell voltage was measured for the membrane electrolyzer after the introduction of the respective solutions in the anode and cathode compartments, followed by application of electric current across the membrane electrolyzer. The foaming was measured for the liquid exiting the cathode compartment. Table II lists cell voltages and presence of caustic foaming for Examples 8–10. These examples used the membrane electrolyzer process outlined above.

Example 8: A lab scale membrane electrolyzer was run for several days under ultra-pure brine solution (30 g of NaCl per 90 g of distilled water) conditions. The cell voltage was stable at 3.25 volts and the caustic product showed no foaming.

Example 9: Byproduct brine solution (30 g of NaCl per 90 g of water) was obtained from a polymer synthesis reaction. This brine contained 6.5 parts per million (ppm) CTAC. by weight of brine solution. When this untreated, CTAC-containing brine was fed to the electrolysis cell, the voltage stabilized at 3.45 volts, which is an elevated value relative to example 8. Further, during this test, the caustic product exhibited foaming.

Example 10: Byproduct brine from Example 9 was treated by passing the brine over a bed of synthetic activated carbon adsorbent (Ambersorb® 572) at room temperature. This treated brine was then fed to the electrolysis cell. For this test, the cell voltage stabilized at 3.25 volts and the caustic product solution did not exhibit foaming.

By comparing the results of examples 8–10, it is clear that treating the CTAC-containing byproduct brine with the pyrolyzed sulfonated polystyrene divinylbenzene (Ambersorb® 572) is effective in lowering the cell voltage and avoiding caustic foaming.

TABLE II

| Example | Test | Cell Voltage (volts) | Caustic Foaming |
|---|---|---|---|
| 8 | Ultra-pure Brine | 3.25 | no |
| 9 | Untreated Reaction Byproduct Brine | 3.45 | yes |
| 10 | Pyrolyzed Sulfonated Polystyrene Divinylbenzene (Ambersorb ® 572) Treated Reaction Byproduct Brine | 3.25 | no |

The presence of caustic foaming was determined by collecting a sample of the liquid exiting the cathode compartment. If the foaming above the sample liquid surface disappeared within about 10 seconds after sampling, then the solution was considered to be non-foaming. If the foam persisted for more than about 10 seconds, then the solution was considered to be foaming.

What is claimed is:

1. A process to remove halogenated quaternary ammonium salts from brine solution, the halogenated quaternary ammonium salt containing at least one halide group covalently bonded to at least one alkyl group, and having formula I Formula I

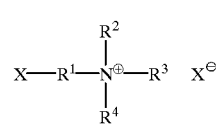

wherein X is selected from the group consisting of Cl, Br, I, and F; $R^1$ represents $C_{1-3}$ alkylene; and $R^2$, $R^3$, and $R^4$ each independently represent a $C_{1-6}$ alkyl radical; the process comprising: contacting the quaternary ammonium salt containing brine solution with an adsorbent at a temperature ranging from about −10 to about 90° C., at a pH from about 1 to about 13, and at a feed rate from about 2 bed volumes to about 40 bed volumes per hour.

2. A process of claim 1 wherein the quaternary ammonium salt concentration is in the range from about 0.5 ppm to 100,000 ppm (10%) by weight of the brine solution.

3. A process of claim 2 wherein the quaternary ammonium salt comprises from about 1 ppm to about 1000 ppm by weight of the brine solution.

4. A process of claim 1 wherein the adsorbent is selected from the group consisting of activated carbon, an ion exchange resin, and a carbonaceous synthetic adsorbent, or mixtures thereof.

5. A process of claim 4 wherein the carbonaceous synthetic adsorbent is pyrolyzed sulfonated polystyrene divinylbenzene.

6. A process of claim 1 wherein the temperature ranges from about 20° C. to about 80° C.

7. A process of claim 1 wherein the pH ranges from about 4 to about 10.

8. A process of claim 1 wherein the feed rate is from about 8 to about 25 bed volumes per hour.

9. A process of claim 1 wherein the quaternary ammonium salt is chloromethyl triethyl ammonium halide.

10. A process according to claim 1 wherein the halogenated quaternary ammonium salt containing brine solution is contacted with an adsorbent at a temperature ranging from about 0° C. to about 80° C., at a pH ranging from about 3 to about 11, and at a feed rate from about 8 bed volumes to about 32 bed volumes per hour.

11. A process according to claim 1 wherein the halogenated quaternary ammonium salt containing brine solution is contacted with an adsorbent at a temperature ranging from about 20° C. to about 80° C., at a pH ranging from about 4 to about 10, and at a feed rate from about 8 bed volumes to about 32 bed volumes per hour.

12. A process to remove halogenated quaternary ammonium salts from brine solution comprising contacting the halogenated quaternary ammonium salt containing brine solution with a synthetic activated carbon adsorbent, said quaternary ammonium salt having formula I Formula I

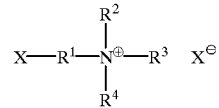

wherein X is selected from the group consisting of Cl, Br, I, and F; $R^1$ represents $C_{1-3}$ alkylene; and $R^2$, $R^3$, and $R^4$ each independently represent a $C_{1-6}$ alkyl radical.

13. The process of claim 12, wherein the halogenated quaternary ammonium salt is a chloro-alkyl quaternary ammonium salt.

14. The process of claim 12, wherein the halogenated quaternary ammonium salt is chloromethyl triethylammonium halide.

15. The process of claim 12, wherein the halogenated quaternary ammonium salt is chloromethyl triethylammonium chloride.

* * * * *